United States Patent [19]

Knowles et al.

[11] Patent Number: 5,798,219
[45] Date of Patent: Aug. 25, 1998

[54] SEROLOGICAL IDENTIFICATION OF CATTLE, SHEEP OR GOATS INFECTED WITH ANAPLASMA SPECIES

[75] Inventors: Donald P. Knowles; Travis C. McGuire; Guy H. Palmer; William C. Davis; Terry F. McElwain, all of Pullman, Wash.

[73] Assignees: The United States of America as represented by the Secretary of Agriculture, Washington, D.C.; Washington State University Research Foundation, Pullman, Wash.

[21] Appl. No.: 730,995

[22] Filed: Oct. 16, 1996

Related U.S. Application Data

[63] Continuation of Ser. No. 156,426, Nov. 23, 1993, abandoned.

[51] Int. Cl.$^6$ .................................................. G01N 33/53
[52] U.S. Cl. ..................... 435/7.93; 435/70.21; 435/340; 530/388.4
[58] Field of Search .................................. 435/7.1, 7.22, 435/7.9, 7.92, 7.93, 70.21, 332, 340; 436/518; 530/388.1, 388.2, 388.6, 388.4

[56] References Cited

U.S. PATENT DOCUMENTS 4,134,792  1/1979  Boguslaski et al. .

OTHER PUBLICATIONS

Visser et al, Infect Immun, Dec. 1992, 60 (12):5139–5144.
Anderson, Journal of Immunological Methods, 1984, 74: 139–149.
Tebele et al, Infect Immun, Sep. 1991, 59(9): 3199–3204.
Harlow et al, "Antibodies: A Laboratory Manual", 1988 by Cold Spring Harbor Labs (N.Y) pp. 511–552.
Palmer et al, International Journal For Parasitology, 1988, 18(1):3149–3204.
Harlow et al, "Antibodies: A Laboratory Manual", Cold Spring Harbor Press 1988 p. 342.

*Primary Examiner*—Paula Hutzell
*Assistant Examiner*—Patricia A. Duffy
*Attorney, Agent, or Firm*—M. Howard Silverstein; John D. Fado; Margaret A. Connor

[57] ABSTRACT

The subject invention concerns the use of monoclonal antibody ANAF16C1 and Anaplasma species major surface protein-5 in the competitive inhibition format for the serological identification of animals infected with Anaplasma species.

4 Claims, 2 Drawing Sheets

SEROLOGICAL IDENTIFICATION OF CATTLE, SHEEP OR GOATS INFECTED WITH ANAPLASMA SPECIES

This application is a continuation of application Ser. No. 08/156,426, filed Nov. 23, 1993 now abandoned.

FUNDING: U. S. Department of Agriculture Cooperative Agreement-58-5348-1-178 & U. S. Department of Agriculture Cris Work Unit 5348-32000-009-00D.

BACKGROUND OF THE INVENTION

Anaplasmosis, a vector-borne rickettsial disease of cattle, sheep and goats is caused by three species: *Anaplasma marginale, Anaplasma centrale* and *Anaplasma ovis*. Clinical disease is characterized by anemia, weight loss, abortion and death. Survivors are lifelong carriers of the rickettsia. Eventual control of Anaplasma species infection will require both an effective vaccine and identification of carrier cattle, sheep or goats. Two possible methods for routine carrier identification are a nucleic acid probe for hybridization of infected blood or the detection of Anaplasma species-specific antibody in serum. Hybridization of DNA extracted from blood with an *Anaplasma marginale*-specific nucleic acid probe does not always detect known carriers, because of cyclic changes in rickettsemia levels. Carrier identification by antibody requires that infected animals never clear the rickettsia. Indefinite persistence of *Anaplasma marginale* in infected cattle has been documented. Current serologic tests for anaplasmosis are not widely used, primarily because the error rate is high. One problem with current tests is false positive results caused by erythrocyte contamination of the *Anaplasma marginale* antigen used in the tests, and the presence of anti-erythrocyte antibody in the sera of some cattle.

Recently, progress has been made toward the characterization of a surface membrane protein of *Anaplasma marginale* for use in diagnosis (N. Tebele, T. C. McGuire, T. C., and G. H. Palmer, Infect. Immun. 59:3199-3204, 1991 and E. S. Visser, McGuire, T. C., Palmer, G. H., Davis, W. C., Shkap, V., Pipano, E. and D. P. Knowles, jr., Infect. Immun 60:5139-5144, 1992.). This protein, designated major surface protein 5 (MSP-5) and monoclonal antibody ANAF16C1 were shown to have utility when used together in the competitive inhibition enzyme-linked immunosorbent assay (CI-ELISA) format (Anderson, J. Immunol. Meth., 74:139-149, 1984) for the diagnosis of cattle, sheep and goats infected with *Anaplasma marginale, Anaplasma centrale* or *Anaplasma ovis* (E. S. Visser, McGuire, T. C., Palmer, G. H., Davis, W. C., Shkap, V., Pipano, E. and D. P. Knowles, jr., Infect. Immun 60:5139-5144, 1992.).

BRIEF SUMMARY OF THE INVENTION

Disclosed and claimed here is a CI-ELISA using monoclonal antibody ANAF16C1 and the corresponding protein, *Anaplasma marginale* major surface protein-5, bound by monoclonal antibody ANAF16C1 for the identification of cattle, sheep or goats persistently infected with *Anaplasma marginale, Anaplasma centrale*, or *Anaplasma ovis*. This invention provides a means of identifying cattle, sheep; or goats that are persistently infected with *Anaplasma marginale, Anaplasma centrale* or *Anaplasma ovis*. This test is specific for Anaplasma species detection since the specificity of this CI-ELISA resides solely in monoclonal antibody ANAF16C1 and monoclonal antibody ANAF16C1 as been shown to specifically bind to only Anaplasma species MSP-5. Since MSP-5 is conserved in all known Anaplasma species, it is logical to assert that MSP-5 is conserved in all isolates of Anaplasma species.

BRIEF DESCRIPTION OF THE DRAWINGS

SEQ ID NO:1 is the DNA sequence of *Anaplasma marginale* major surface protein 5.

SEQ ID NO:2 is the amino-acid sequence of Anaplasma marginale major surface protein 5.

BRIEF DESCRIPTION OF THE SEQUENCES

SEQ ID NO. 1 is the DNA sequence of *Anaplasma marginale* major surface protein

SEQ ID NO. 2 is the amino acid sequence of *Anaplasma marginale* major surface protein 5.

DETAILED DESCRIPTION OF THE INVENTION

Figure 2:
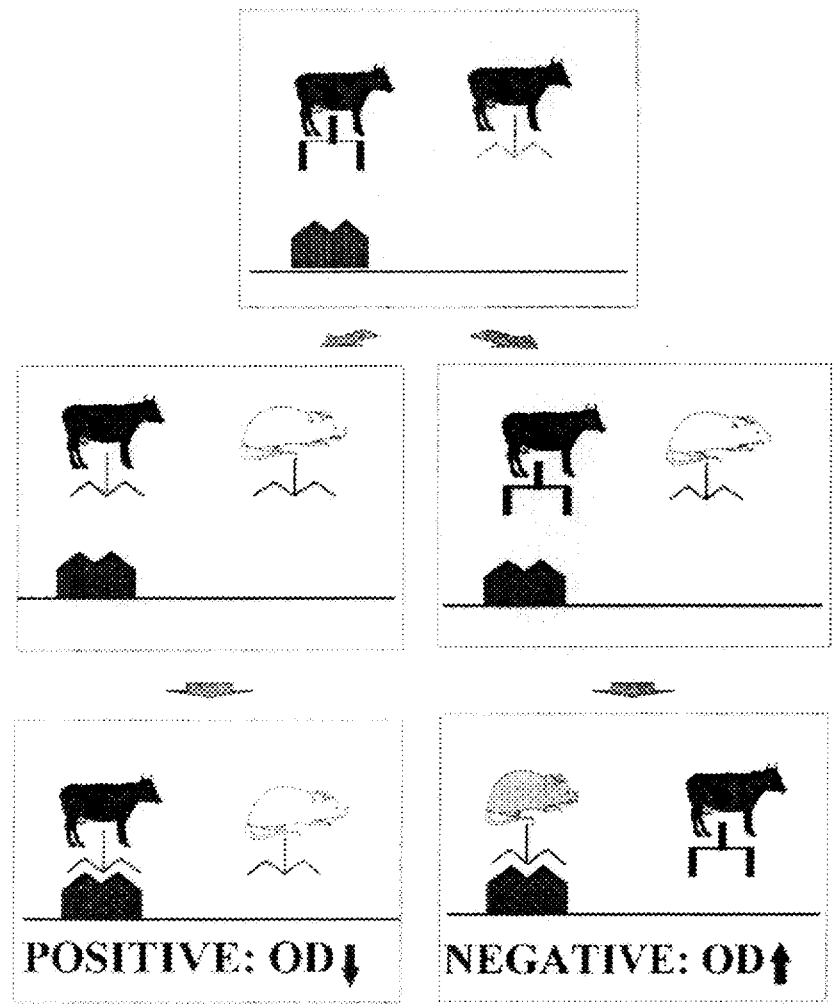
FIG. 2 is a diagram of the CI-ELISA using monoclonal antibody ANAF16C1 (mouse), *Anaplasma marginale* major surface protein 5 (▲▲), and test serum (cow).

The subject invention pertains to the use of monoclonal antibody ANAF16C1 and Anaplasma major surface protein 5 in a CI-ELISA format (FIG. 2) for the serological detection of cattle, sheep or goats infected with *Anaplasma marginale, Anaplasma centrale* or *Anaplasma ovis*. Hybridoma ANAF16C1 which produces and secrets monoclonal antibody ANAF16C1 was deposited on Dec. 2, 1997, with the American Type Culture Collection (ATCC), 12301 Parklawn Drive, Rockville, Md. 20852 USA, under terms of the Budapest Treaty, and has been assigned the accession number ATCC HB-12440.

Figure 1:
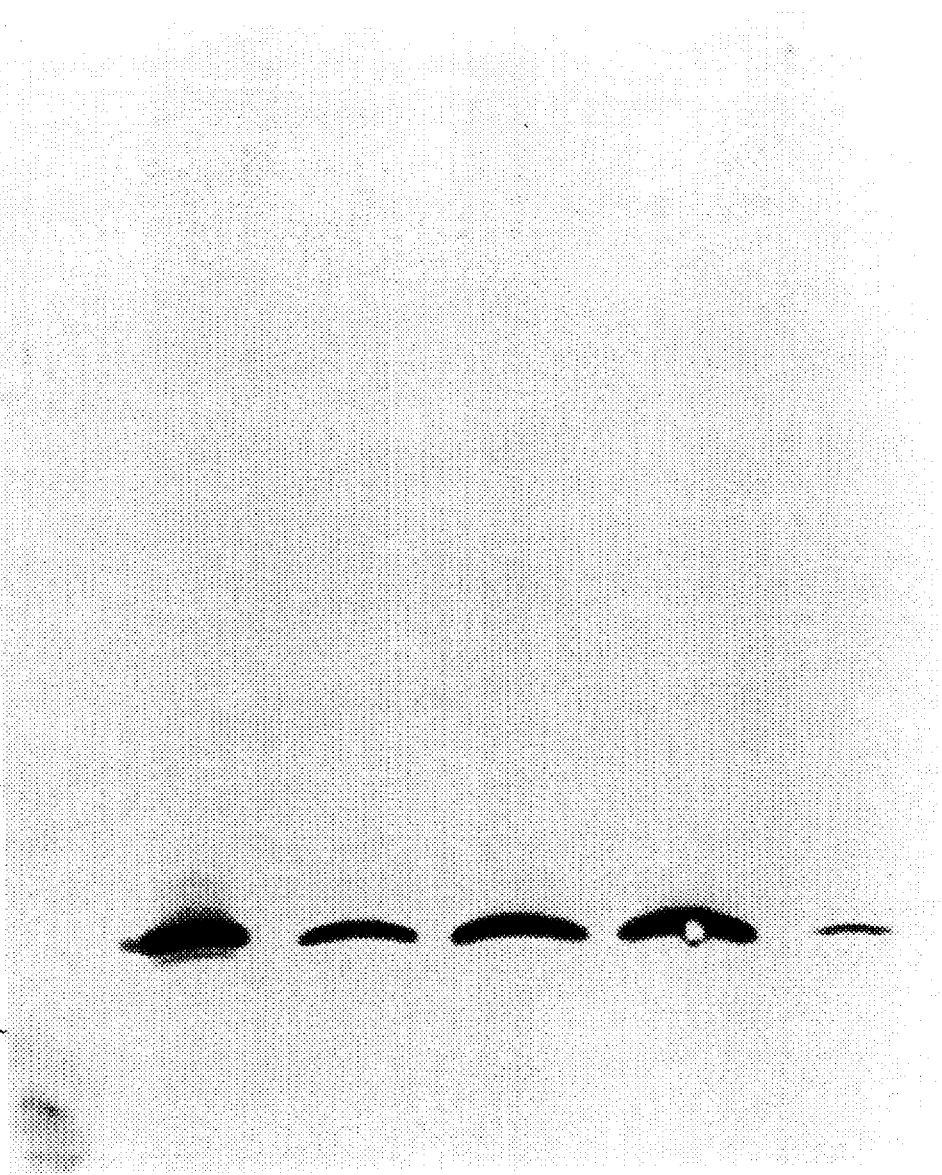
FIG. 1 is an immunoblot demonstrating the binding of monoclonal antibody ANAF16C1 to major surface protein 5 of: Florida strain of *Anaplasma marginale* (lane 2); Israeli strain of *Anaplasma centrale* (lane 4); Israeli non-tailed strain of *Anaplasma marginale* (lane 6); Israeli tailed strain of *Anaplasma marginale* (lane 8), and Idaho strain of *Anaplasma ovis* (lane 10).

The evidence that MSP-5 is effective in the CI-ELISA format for the diagnosis of animals infected with Anaplasma species are:

(i) MSP-5 is conserved in all known Anaplasma species (FIG. 1);

(ii) all immune sera tested from animals infected with Anaplasma species bind to MSP-5, and (iii) all immune sera tested from animals infected with Anaplasma species compete with monoclonal antibody ANAF16C1 for binding to MSP-5.

The evidence that monoclonal antibody ANAF16C1 is effective in the CI-ELISA format for the diagnosis of animals infected with Anaplasma species are: (i) monoclonal antibody ANAF16C1 binds to MSP-5 in all known Anaplasma species; (ii) monoclonal antibody ANAF16C1 binds to both native and recombinant MSP-5, and (iii) all immune sera tested from animals infected with Anaplasma species compete with monoclonal antibody ANAF16C1 for binding to MSP-5.

MATERIALS AND METHODS

The Florida strain of *Anaplasma marginale* from which native and recombinant MSP-5 were derived originated from a pooled blood sample collected from naturally infected cattle in various sections of Florida in 1955 (Ristic, M. and C. A. Carson, In L. H. Miller, J. A. Pino, and J. J.

McKelvey (ed.), Immunity to blood parasites of animals and man. Plenum Publishing Corp., New York, 1977).

Native MSP-5 was obtained from blood stabilates by differential centrifugation as described (Palmer, G. H. and T. C. McGuire, J. Immun. 133:1010–1015, 1984). Briefly, 20 milliliters of stabilate was thawed at 37° C. for 10 min and then washed 3 times by suspension in 40 ml of RPMI 1640 media (Flow Laboratories, McLean, Va.) containing 2 mM 1-Glutamine and 25 mM HEPES, with centrifugation at 27,000×G. The sediment was resuspended in 35 ml of media, disrupted by 2 min of sonication at 50 W (127×4 mm titanium probe, Braun-Sonic 1510; Braun Instruments, San Francisco, Calif.), and was washed two times at 1650 ×G for 15 min.

Recombinant MSP-5 (SEQ ID NO:2) was prepared from a 50-ml overnight culture of E. coli XL1-Blue containing pAM104 in LB broth with 50 ug of ampicillin per ml. Molecular clone pAM104 contains the msp5 gene with the nucleotide sequence of MSP-5 presented in SEQ ID NO:1. A bacterial lysate prepared with PI buffer (50 mM Tris [pH 8.0], 5 mM EDTA, 5 mM iodoacetamide, 0.1 mM N-a-p-tosyl-L-lysine chloromethyl ketone 1 mM phenylmethylsulfonyl fluoride, 1 mg of lysozyme per ml, 1% Nonidet P-40).

Monoclonal antibody ANAF16C1 was made by fusing X63-Ag8.653 murine myeloma cells (J. F. Kearney, Radbruch, A., Liesegang, B. and K. Rajewsky J. Immunol. 123:1548–1550, 1979) with spleen cells from BALB/c mice immunized with purified initial bodies of the Florida strain of Anaplasma marginale. An immunoglobulin G2a monoclonal antibody that immunoprecipitated a 19 kDa protein from 125I-surface-radiolabeled solubilized initial bodies was designated ANAF16C1. Monoclonal antibody ANAF16C1 was conjugated with horseradish peroxidase as described (A. G. Farr and P. K. Nakane, J. Immun. Meth. 47:129–144, 1981).

The CI-ELISA format was first described in 1984 (J. Anderson, J. Immunol. Meth., 74:139–149, 1984). An overview of the use of the CI-ELISA format for the detection of animals infected with Anaplasma species is as follows: (i) Immulon 2 plates are coated with native or recombinant MSP-5, (ii) plate is incubated overnight at RT; (iii) the plate is rinsed and blocker is added (1 hour); (iv) test sera are incubated with antigen (15 min); (v) monoclonal antibody ANAF16C1 conjugated to horseradish peroxidase is added and incubated for 15 min; (vi) wells are rinsed and substrate (p-nitrophenyl phospate) is added (10 min), and vii) the reaction is stopped and the optical densisty is read at 490.

The specifics of the CI-ELISA using monoclonal antibody ANAF16C1 and MSP-5 for serological detection of animals infected with Anaplasma species are as follows. Preparation of all buffers and reagents are provided below. Wells of an Immulon 2 plate (Dynatech Laboratories, Chantilly, Va.) are coated with sufficient native or recombinant MSP-5 to provide an $OD_{490}$ reading of between 1.0 and 1.5. The appropriate dilution of initial body lysate (native msp-5) or bacterial lysate applied to an Immulon 2 plate (recombinant MSP-5) is determined by titration with monoclonal antibody ANAF16C1. After plates are coated with the appropriate amount of MSP-5 lysate, the Immulon 2 plates are sealed with acetate and incubated overnight at room temperature. The well contents are removed and the wells rinsed once with 200 ul of PBS/Tween. Coated plates are blocked by adding 200 ul blocking buffer, and incubating for 1 hr at room temperature. Blocker is removed from the plates and 40 ul of undiluted test serum is added to each well and incubated for 15 min at room temperature. Conjugated monoclonal antibody ANAF16C1 is then added at the appropriate concentration determined previously by titration. Conjugated monoclonal antibody ANAF16C1 is diluted such that the appropriate quantity of conjugated monoclonal antibody ANAF16C1 is added in 10 ul. The mixture is incubated for 15 min at room temperature. Contents are removed from the wells and the wells are rinsed twice with 200 ul of PBS/Tween and once with substrate buffer. Fifty ul of OPD substrate is added per well and incubated for 10 min at room temperature. The reaction is stopped by adding 25 ul of 3N HCl per well. The $OD_{490}$ is read.

What are claimed are:

1. A method for detecting Anaplasma specific antibodies in an animal, wherein the animal is a ruminant selected from the group consisting of cattle, sheep, and goat, said method comprising:

(a) obtaining a serological sample from the ruminant;

(b) conducting a competitive inhibition enzyme-linked immunosorbent assay on said serological sample using native or recombinant Anaplasma major surface protein 5 and labeled monoclonal antibody ANAF16C1 produced by hybridoma ANAF16C1 deposited with the American Type Culture Collection as accession number ATTC HB-12440;

(c) wherein the presence of competition for binding of said labeled monoclonal antibody to the native or recombinant Anaplasma major surface protein 5 indicates the presence of Anaplasma specific antibodies to major surface protein 5 in the serological sample.

2. The method of claim 1, wherein the label is horseradish peroxidase.

3. A hybridoma cell line ANAF16C1 deposited with the American Type Culture Collection as accession number ATCC HB-12440.

4. A monoclonal antibody ANAF16C1 produced by the hybridoma cell line ANAF16C1 deposited with the American Type Culture Collection as accession number HB-12440.

* * * * *

UNITED STATES PATENT AND TRADEMARK OFFICE
CERTIFICATE OF CORRECTION

PATENT NO. : 5,798,219
DATED : August 25, 1998
INVENTOR(S) : Donald P. Knowles et al.

It is certified that error appears in the above-identified patent and that said Letters Patent is hereby corrected as shown below:

<u>Columns 5 and 6,</u>
In SEQ ID NO:1, change nucleotide 594 from "C" to -- G --.

Signed and Sealed this

Seventeenth Day of June, 2003

JAMES E. ROGAN
*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1146 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Anaplasma marginale
        ( C ) INDIVIDUAL ISOLATE: Florida ( x i ) SEQUENCE DESCRIPTION: SEQ ID NO:1:

```
GTATACTCAG  TTGCGCCTGG  CGCTTGACCA  ACCTGGGCAT  AGGTGCTACG  ATCGCGCCTG      60
CTCGTTTTGC  CGTCCGGCAA  TGTGGCGCAT  TTTTGAGTGT  TCGTTGGGGT  GTGATAGATG     120
```

-continued

```
AGAATTTTCA AGATTGTGTC TAACCTTCTG CTGTTCGTTG CTGCCGTGTT CCTGGGGTAC     180
TCCTATGTGA ACAAGAAAGG CATTTCAGC AAAATCGGCG AGAGGTTTAC CACTTCCGAA      240
GTTGTAAGTG AGGGCATAGC CTCCGCGTCT TTCAACAATT TGGTTAATCA CGAGGGGTC      300
ACCGTCAGTA GCGGCGATTT TGGCGGCAAG CACATGTTGG TAATATTCGG CTTCTCAGCC     360
TGTAAGTACA CGTGCCCTAC CGAGTTAGGC ATGGCTTCTC AGCTCCTAAG TAAACTAGGC     420
GACCATGCCG ATAAGTTGCA AGTTGTGTTC ATAACTGTTG ATCCGAAAAA TGACACCGTA     480
GCCAAGCTTA AAGAGTACCA CAAGTCTTTT GATGCGAGAA TTCAGATGCT CACAGGCGAA     540
GAAGCAGACA TAAAGAGCGT GGTTGAAAAC TACAAGGTGT ATGTGGGCGA CAACAAGCCA     600
AGTGATGGTG ATATCGACCA CTCAACGTTC ATGTACCTCA TCAATGGGAA AGGCAGGTAT     660
GTCGGGCATT TTGCGCCAGA TTTTAACGCG TCTGAGGGCC AAGGCGAGGA GCTGTTTAAG     720
TTTGTCAGCG GTCACATGCT TAATTCTTAG TTAAGCATGG CAGTGGTACA GTTTCGTGTG     780
TCGGTCGTCC TTGTGAGGCA GTAGAAAGTA TGGGGCTTTG GGGGCTTTCC TTTGTGGCGT     840
TTGTCGCGCT TGCGTTAGGA GCTGGGGCTG ACCAGATCAG GGTGGTTGGC TCTTCCACCG     900
TGTTCCCATT TATCTCTTCT GTTGCCGAAG AGTTTGGTAG ATTCTCCGCC TATAGAACCC     960
CCGTCATAGA GTCCGTGGGA AGTGGCATGG GCTTTAACAT GTTTTGCGCT GGCAGCAGCA    1020
GTGATACACC AGACATAGCC ATGTCCTCTA GGCGCATCAA GGATGCAGAA GTCGAACTTT    1080
GCGGCATGAA TGGCGTGAAG GACATGATCG AGATAGGTCT GGGCTACGAC GGCATAGCCC    1140
GAATTC                                                               1146
```

( 2 ) INFORMATION FOR SEQ ID NO:2:

( i ) SEQUENCE CHARACTERISTICS:
( A ) LENGTH: 210 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( x i ) SEQUENCE DESCRIPTION: SEQ ID NO:2:

```
Met Arg Ile Phe Lys Ile Val Ser Asn Leu Leu Phe Val Ala Ala
 1               5                  10                  15

Val Phe Leu Gly Tyr Ser Tyr Val Asn Lys Lys Gly Ile Phe Ser Lys
             20                  25                  30

Ile Gly Glu Arg Phe Thr Thr Ser Glu Val Val Ser Glu Gly Ile Ala
             35                  40                  45

Ser Ala Ser Phe Asn Asn Leu Val Asn His Glu Gly Val Thr Val Ser
     50                  55                  60

Ser Gly Asp Phe Gly Gly Lys His Met Leu Val Ile Phe Gly Phe Ser
 65                  70                  75                  80

Ala Cys Lys Tyr Thr Cys Pro Thr Glu Leu Gly Met Ala Ser Gln Leu
                     85              90                  95

Leu Ser Lys Leu Gly Asp His Ala Asp Lys Leu Gln Val Val Phe Ile
                 100                 105                 110

Thr Val Asp Pro Lys Asn Asp Thr Val Ala Lys Leu Lys Glu Tyr His
             115                 120                 125

Lys Ser Phe Asp Ala Arg Ile Gln Met Leu Thr Gly Glu Glu Ala Asp
         130                 135                 140

Ile Lys Ser Val Val Glu Asn Tyr Lys Val Tyr Val Gly Asp Lys Lys
```

-continued

| | | | | 145 | | | | | 150 | | | | | 155 | | | | | 160 |
|---|---|---|---|---|---|---|---|---|---|---|---|---|---|---|---|---|---|---|---|
| Pro | Ser | Asp | Gly | Asp 165 | Ile | Asp | His | Ser | Thr 170 | Phe | Met | Tyr | Leu | Ile 175 | Asn |
| Gly | Lys | Gly | Arg 180 | Tyr | Val | Gly | His | Phe 185 | Ala | Pro | Asp | Phe | Asn 190 | Ala | Ser |
| Glu | Gly | Gln 195 | Gly | Glu | Glu | Leu | Phe 200 | Lys | Phe | Val | Ser | Gly 205 | His | Met | Leu |
| Asn | Ser 210 | | | | | | | | | | | | | | |